US012805862B1

(12) United States Patent
Chisholm

(10) Patent No.: US 12,805,862 B1
(45) Date of Patent: Nov. 24, 2026

(54) WOUND CLOSURE SYSTEM

(71) Applicant: Joe Chisholm, Lytle, TX (US)

(72) Inventor: Joe Chisholm, Lytle, TX (US)

( * ) Notice: Subject to any disclaimer, the term of this patent is extended or adjusted under 35 U.S.C. 154(b) by 140 days.

(21) Appl. No.: 18/809,468

(22) Filed: Aug. 20, 2024

(51) Int. Cl.
*A61B 17/04* (2006.01)

(52) U.S. Cl.
CPC .. *A61B 17/0487* (2013.01); *A61B 2017/0495* (2013.01)

(58) Field of Classification Search
CPC ................ A61B 17/04; A61B 17/0487; A61B 2017/0495
See application file for complete search history.

(56) References Cited

U.S. PATENT DOCUMENTS

| | | | | |
|---|---|---|---|---|
| 6,120,525 | A | 9/2000 | Westcott | |
| 6,471,715 | B1 | 10/2002 | Weiss | |
| D629,513 | S | 12/2010 | Bierman | |
| 8,021,341 | B2 | 9/2011 | Lampropoulos | |
| 8,585,737 | B2 | 11/2013 | Moehrle | |
| 10,925,596 | B2 | 2/2021 | Wilke | |
| 2009/0149869 | A1 | 6/2009 | Dolhun | |
| 2011/0082475 | A1 * | 4/2011 | Smith ................ | A61B 17/0482 606/144 |
| 2022/0257238 | A1 * | 8/2022 | Khairkhahan ..... | A61B 17/0469 |

FOREIGN PATENT DOCUMENTS

| | | |
|---|---|---|
| WO | 2006031698 | 3/2006 |

* cited by examiner

*Primary Examiner* — Vi X Nguyen
(74) *Attorney, Agent, or Firm* — Kyle A. Fletcher, Esq.

(57) ABSTRACT

The wound closure system is a therapeutic structure that is for use with a patient. The wound closure system is an instrument that applies a suture to a wound on the patient. The wound closure system remains on the patient after the application of the suture. The wound closure system forms a protective barrier that protects the wound of the patient from the environment. The wound closure system incorporates a base plate structure, a lock plate structure, and a suture. The base plate structure forms the protective barrier. The lock plate structure secures the suture to the base plate structure. The suture is a cord that is used in the management of the wound of the patient.

11 Claims, 7 Drawing Sheets

WOUND CLOSURE SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of surgical instruments for suturing wounds. (A61B17/04)

SUMMARY OF INVENTION

The wound closure system is a therapeutic structure. The wound closure system is adapted for use with a patient. The wound closure system is an instrument that applies a suture to a wound on the patient. The wound closure system remains on the patient after the application of the suture. The wound closure system forms a protective barrier that protects the wound of the patient from the environment. The wound closure system comprises a base plate structure, a lock plate structure, and a suture. The base plate structure forms the protective barrier. The lock plate structure secures the suture to the base plate structure. The suture is a cord that is used in the management of the wound of the patient.

These together with additional objects, features and advantages of the wound closure system will be readily apparent to those of ordinary skill in the art upon reading the following detailed description of the presently preferred, but nonetheless illustrative, embodiments when taken in conjunction with the accompanying drawings.

In this respect, before explaining the current embodiments of the wound closure system in detail, it is to be understood that the wound closure system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the wound closure system.

It is therefore important that the claims be regarded as including such equivalent construction insofar as they do not depart from the spirit and scope of the wound closure system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention.

They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word “exemplary” or “illustrative” means “serving as an example, instance, or illustration.” Any implementation described herein as “exemplary” or “illustrative” is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
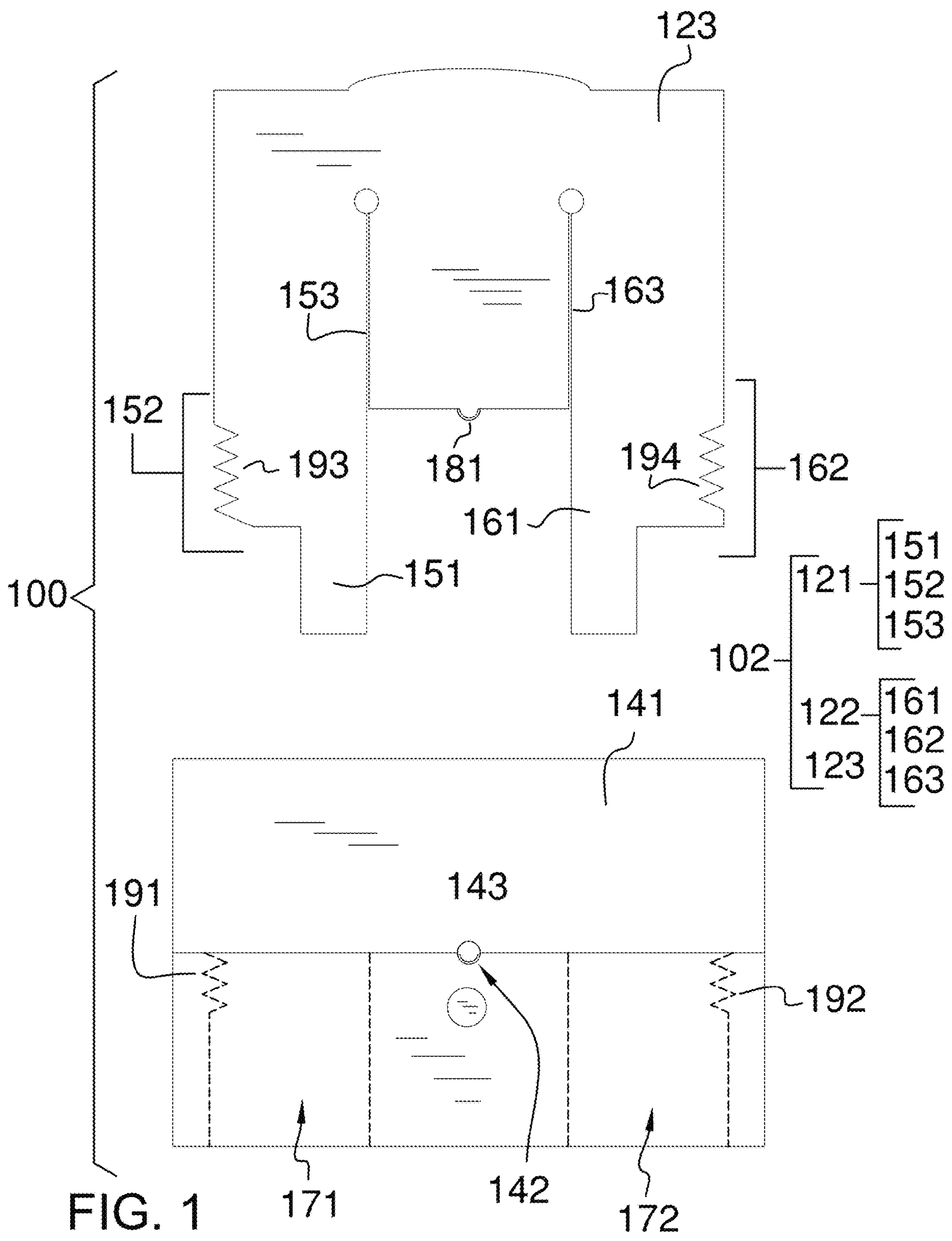
FIG. 1 is a front view of an embodiment of the disclosure.
Figure 2:
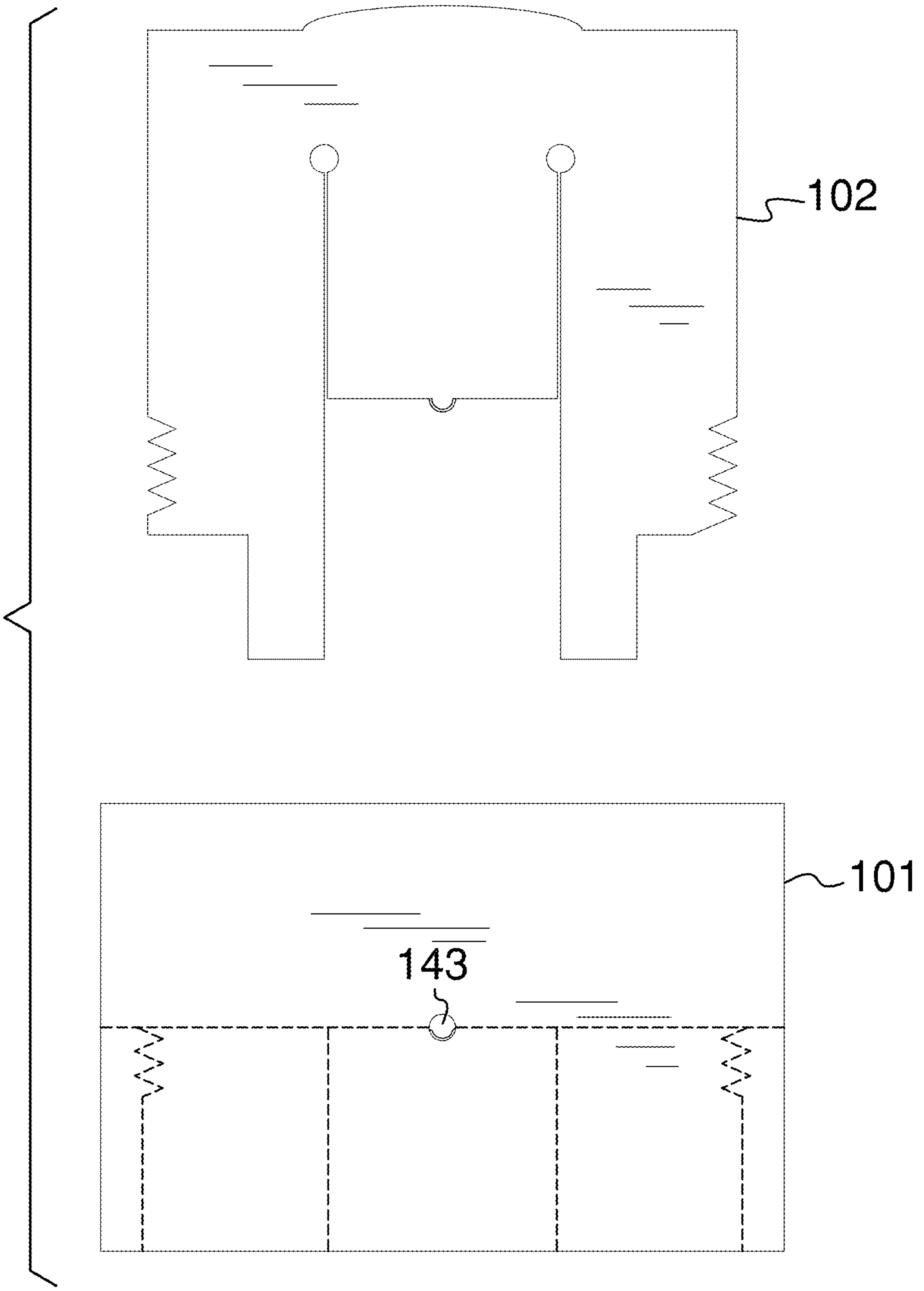
FIG. 2 is a rear view of an embodiment of the disclosure.
Figure 3:
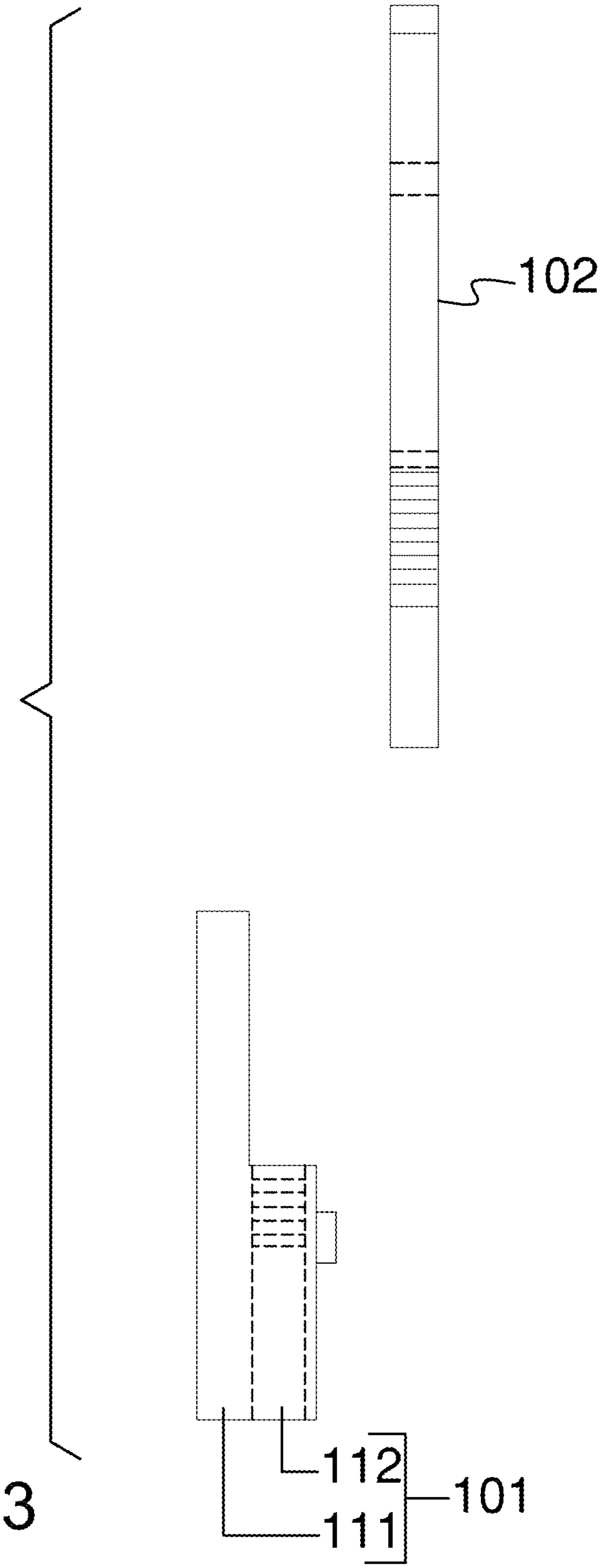
FIG. 3 is a side view of an embodiment of the disclosure.
Figure 4:
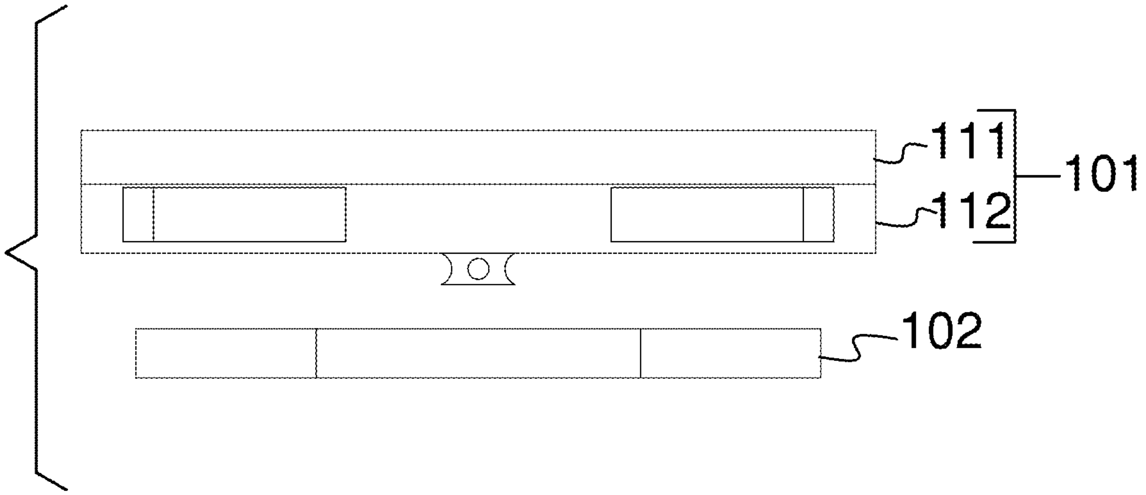
FIG. 4 is a top view of an embodiment of the disclosure.
Figure 5:
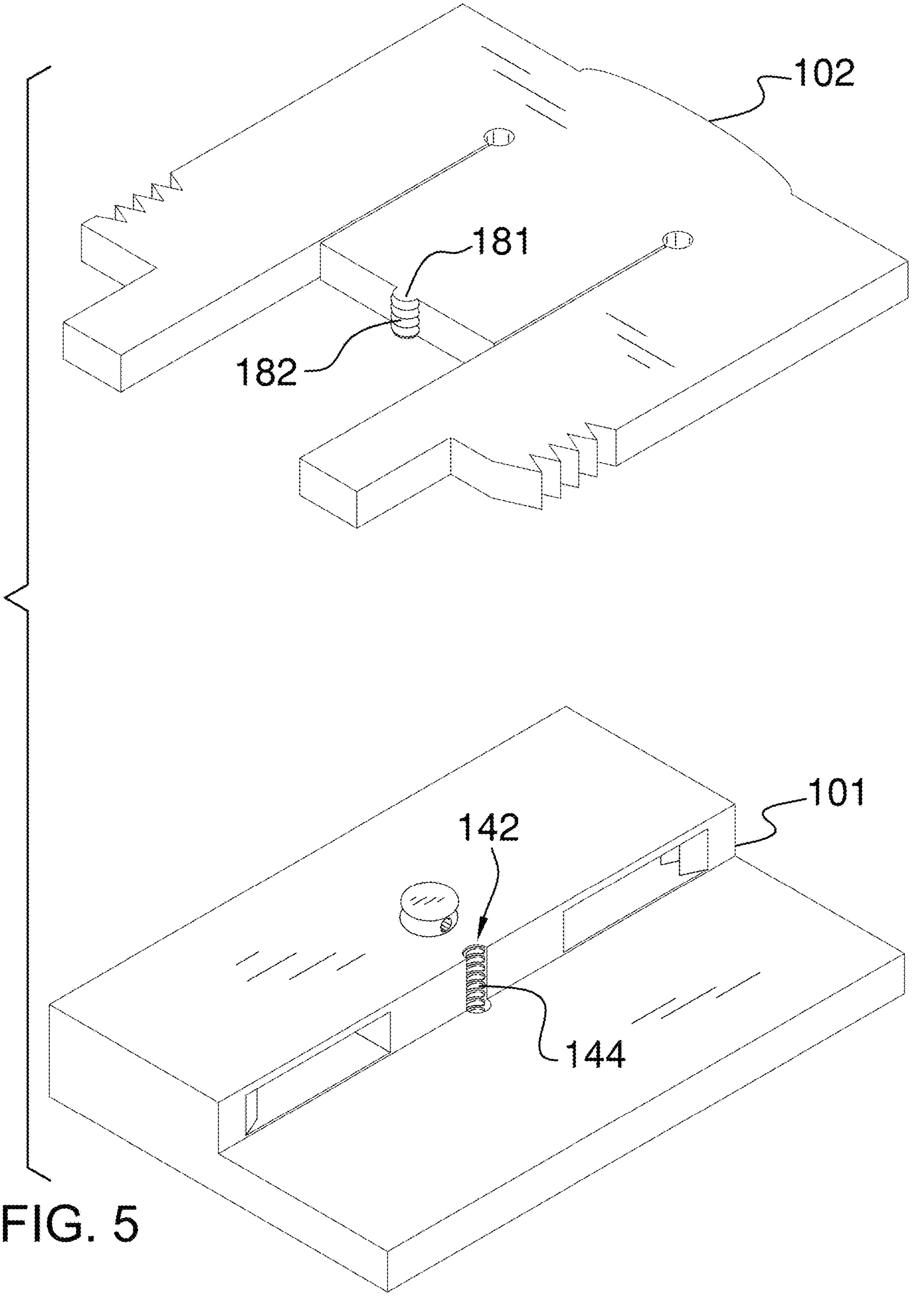
FIG. 5 is a perspective view of an embodiment of the disclosure.
Figure 6:
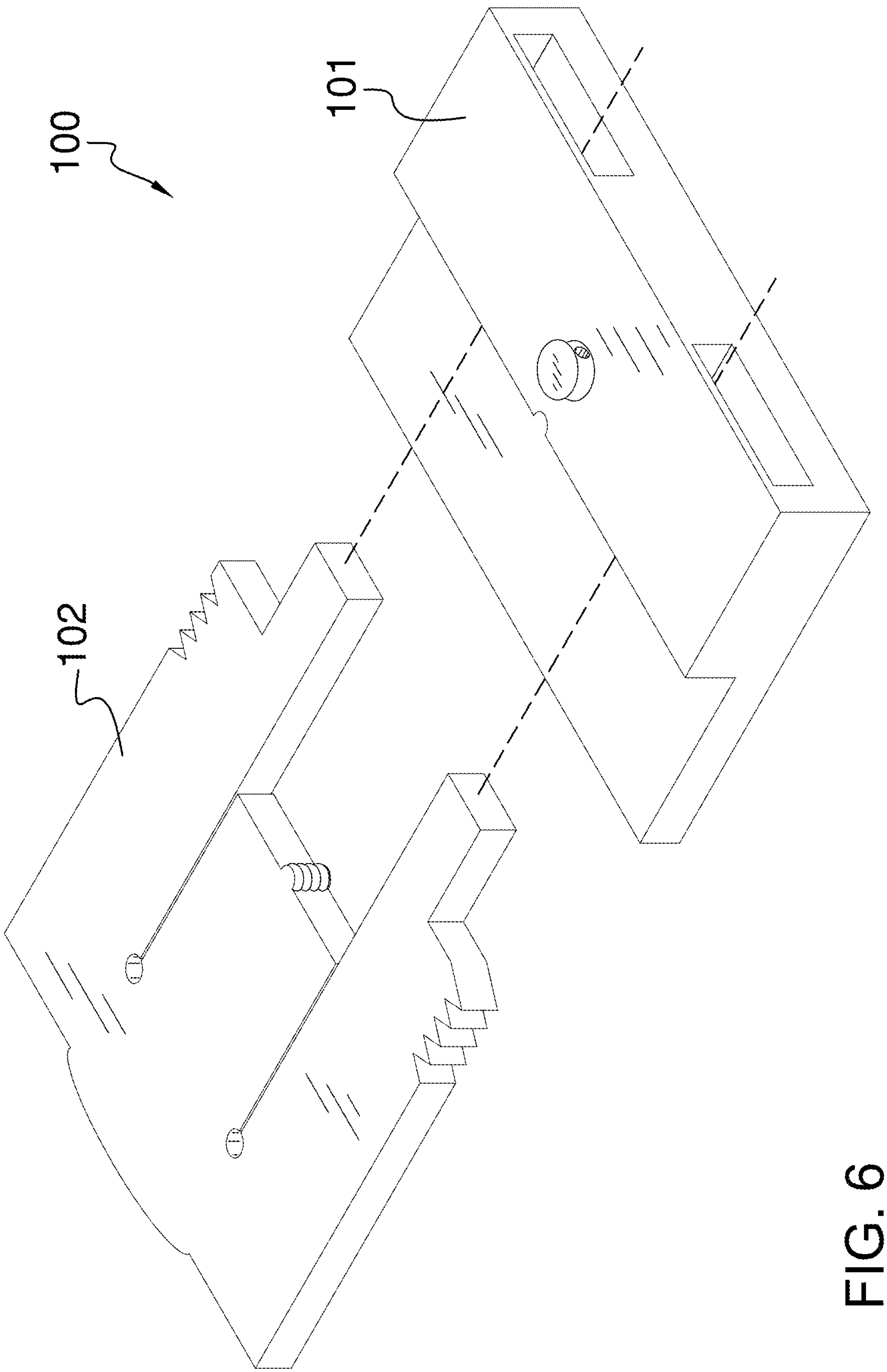
FIG. 6 is an exploded view of an embodiment of the disclosure.
Figure 7:
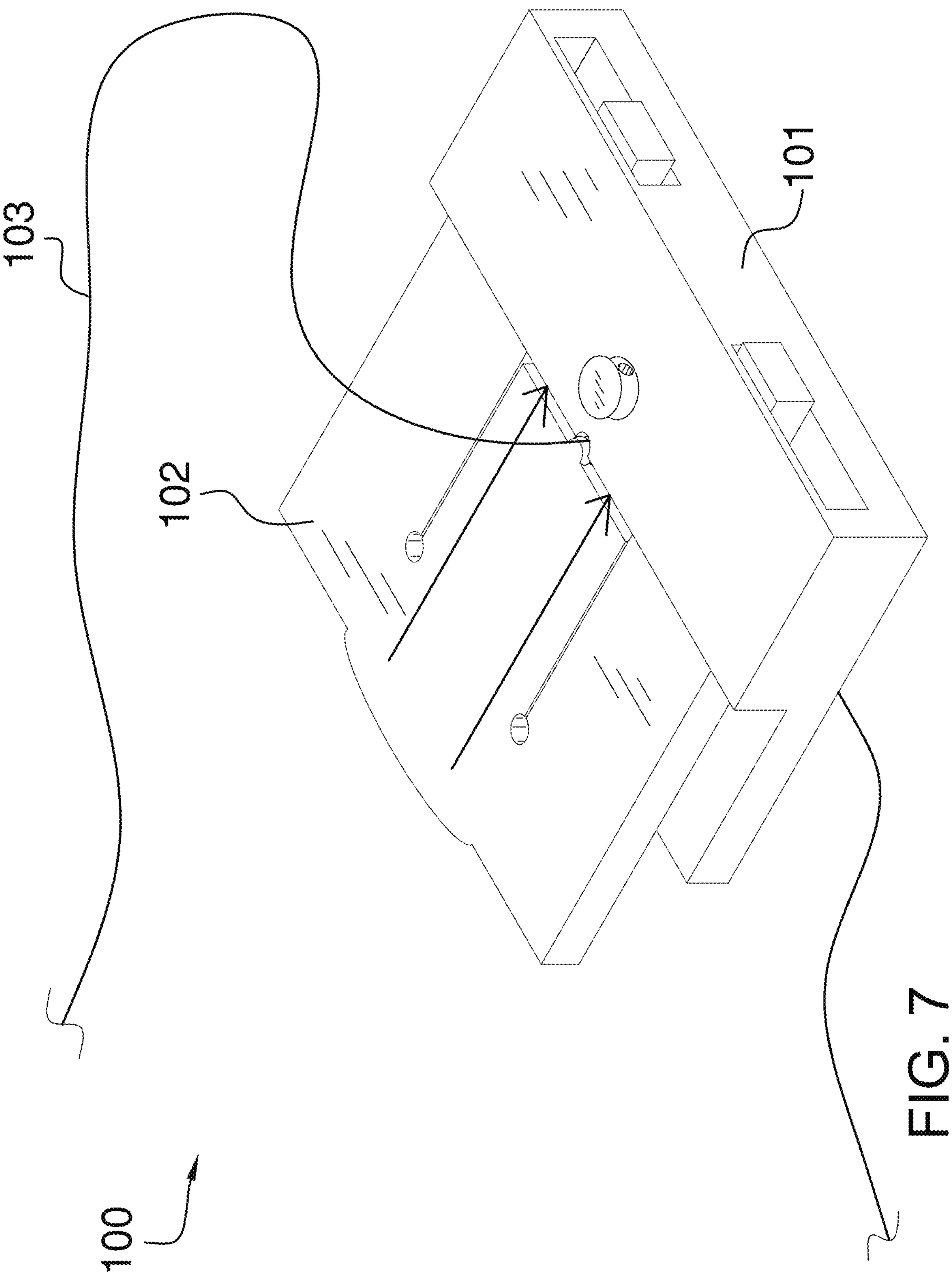
FIG. 7 is an in-use view of an embodiment of the disclosure.

Detailed reference will now be made to one or more potential embodiments of the disclosure, which are illustrated in FIGS. 1 through 7.

The wound closure system 100 (hereinafter invention) is a therapeutic structure. The invention 100 is adapted for use with a patient. The invention 100 is an instrument that applies a suture 103 to a wound on the patient. The invention 100 remains on the patient after the application of the suture 103. The invention 100 forms a protective barrier that protects the wound of the patient from the environment. The invention 100 comprises a base plate structure 101, a lock plate structure 102, and a suture 103. The base plate structure 101 forms the protective barrier. The lock plate structure 102 secures the suture 103 to the base plate structure 101. The suture 103 is a cord that is used in the management of the wound of the patient.

The suture 103 is a cord. The suture 103 forms a sewn seam used to close the wound of the patient. The suture 103 inserts through the base plate structure 101. The lock plate structure 102 presses the suture 103 against the base plate structure 101 to form a tight fit.

The base plate structure 101 forms the structure that is placed against the wound of the patient. The lock plate structure 102 inserts into the base plate structure 101. The lock plate structure 102 secures the suture 103 to the base plate structure 101. The base plate structure 101 has the shape of a stack of disk shaped structures. The base plate structure 101 comprises a ledge plate structure 111 and an anchor plate structure 112.

The ledge plate structure 111 is a prism shaped structure. The ledge plate structure 111 has a disk shape. The ledge plate structure 111 is the structure of the base plate structure 101 that rests on the wound of the patient.

The anchor plate structure 112 is a prism shaped structure. The anchor plate structure 112 has a disk shape. The span of the length of the perimeter of the congruent ends of the disk structure of the anchor plate structure 112 is lesser than the span of the length of the perimeter of the congruent ends of the disk structure of the ledge plate structure 111. A congruent end of the disk structure of the anchor plate structure 112 permanently attaches to the congruent end of the disk structure of the ledge plate structure 111 that is distal from the wound of the patient. The anchor plate structure 112 forms the structure of the base plate structure 101 that receives the lock plate structure 102 for attachment. The anchor plate structure 112 comprises an anchor plate disk 141, a suture 103 notch 142, and a suture 103 eye 143.

The anchor plate disk 141 is a prism shaped structure. The anchor plate disk 141 is a disk shaped structure. The anchor plate disk 141 forms the physical disk structure of the anchor plate structure 112. The anchor plate disk 141 permanently attaches to the congruent end of the disk structure of the ledge plate structure 111. The anchor plate disk 141 further comprises a first anchor mortise 171 and a second anchor mortise 172.

The first anchor mortise 171 is a mortise that is formed into the lateral face of the disk structure of the anchor plate structure 112. The first anchor mortise 171 is sized such that the first lock plate tenon structure 121 of the lock plate structure 102 inserts into the first anchor mortise 171. The first anchor mortise 171 is formed with a locking mechanism that locks the ledge plate structure 111 into a fixed position relative to the first anchor mortise 171. The first anchor mortise 171 further comprises a first plurality of lock teeth 191. The first plurality of lock teeth 191 is a set of teeth that are formed on the interior surface of the first anchor mortise 171. The first plurality of lock teeth 191 forms the locking mechanism of the first anchor mortise 171.

The second anchor mortise 172 is a mortise that is formed into the lateral face of the disk structure of the anchor plate structure 112. The second anchor mortise 172 is sized such that the second lock plate tenon structure 122 of the lock plate structure 102 inserts into the second anchor mortise 172. The second anchor mortise 172 is formed with a locking mechanism that locks the ledge plate structure 111 into a fixed position relative to the second anchor mortise 172. The second anchor mortise 172 further comprises a second plurality of lock teeth 192. The second plurality of lock teeth 192 is a set of teeth that are formed on the interior surface of the second anchor mortise 172. The second plurality of lock teeth 192 forms the locking mechanism of the second anchor mortise 172.

The suture 103 eye 143 is a negative space that is formed through the congruent ends of the disk structure of the ledge plate structure 111. The suture 103 inserts through the suture 103 eye 143 from the wound of the patient into the suture 103 notch 142.

The suture 103 notch 142 is a notch that is formed in the lateral face of the disk structure of the anchor plate disk 141. The suture 103 notch 142 is positioned between the first anchor mortise 171 and the second anchor mortise 172. The suture 103 is pressed by the lock plate structure 102 into the suture 103 notch 142 of the anchor plate structure 112.

The suture 103 notch 142 further comprises an interior surface thread structure 144. The interior surface thread structure 144 comprises a plurality of negative spaces that are formed in the interior face of the suture 103 notch 142. Each negative space selected from the plurality of negative spaces forms a non-Euclidean prism shape. Each negative space selected from the plurality of negative spaces forms a non-Euclidean prism shape is formed in the interior non-Euclidean surface of the suture 103 notch 142. The form factor of any initially selected negative space is identical to the form factor of any subsequently selected negative space. The center axis of any initially selected negative space is parallel to the center axis of any subsequently selected negative space. The center axes of the plurality of negative spaces are evenly spaced.

The lock plate structure 102 is a prism shaped structure. The lock plate structure 102 is formed as a disk. The lock plate structure 102 has an irregular prism shape. The lock plate structure 102 inserts into the base plate structure 101. The forms factor of the lock plate structure 102 fits flush against the base plate structure 101. The lock plate structure 102 inserts into the base plate structure 101 such that the suture 103 inserts into the lock plate structure 102 and the base plate structure 101. The suture 103 inserts between the base plate structure 101 and the lock plate structure 102. The suture 103 is held in a fixed position relative to the lock plate structure 102 and the base plate structure 101 by frictional forces. The lock plate structure 102 comprises a first lock plate tenon structure 121, a second lock plate tenon structure 122, and a lock plate structure 123.

The first lock plate tenon structure 121 is a tenon that secures the lock plate structure 102 to the base plate structure 101. The first lock plate tenon structure 121 inserts into the first anchor mortise 171 of the anchor plate structure 112 of the base plate structure 101. The first lock plate tenon structure 121 is a locking structure. The first lock plate tenon structure 121 interacts with the first anchor mortise 171 such that the first lock plate tenon structure 121 detachably attaches to the first anchor mortise 171. The first lock plate tenon structure 121 locks the lock plate structure 102 into a fixed position relative to the base plate structure 101 and the suture 103. The first lock plate tenon structure 121 comprises a first guide structure 151, a first locking edge 152, a first relief slot 153, and a third plurality of lock teeth 193.

The first guide structure 151 forms the leading structure of the first lock plate tenon structure 121. By leading structure is meant that the first guide structure 151 is the first element of the first lock plate tenon structure 121 that inserts into the first anchor mortise 171 of the anchor plate disk 141 of the anchor plate structure 112. The first guide structure 151 aligns the first lock plate tenon structure 121 with the first anchor mortise 171 such that the first locking edge 152 aligns with the locking structure of the first anchor mortise 171.

The first locking edge 152 is the edge of the first lock plate tenon structure 121 that is distal from the second lock plate tenon structure 122. The first locking edge 152 is the structure of the first lock plate tenon structure 121 that detachably locks the first lock plate tenon structure 121 into a fixed position within the first anchor mortise 171.

The first relief slot 153 is a slit that is formed through the congruent ends of the disk structure of the lock plate structure 123. The first relief slot 153 aligns with the edge of the first guide structure 151. The first relief slot 153 provides a flexibility to the first guide structure 151 that allows the first guide structure 151 to bend as the first guide structure 151 aligns with the locking structure of the first anchor mortise 171.

The second lock plate tenon structure 122 is a tenon that secures the lock plate structure 102 to the base plate structure 101. The second lock plate tenon structure 122 inserts into the second anchor mortise 172 of the anchor plate structure 112 of the base plate structure 101. The second lock plate tenon structure 122 is a locking structure. The second lock plate tenon structure 122 interacts with the second anchor mortise 172 such that the second lock plate tenon structure 122 detachably attaches to the second anchor mortise 172. The second lock plate tenon structure 122 locks the lock plate structure 102 into a fixed position relative to the base plate structure 101 and the suture 103. The second lock plate tenon structure 122 comprises a second guide structure 161, a second locking edge 162, a second relief slot 163, and a fourth plurality of lock teeth 194.

The third plurality of lock teeth 193 is a set of teeth that are formed on the first locking edge 152 of the first lock plate tenon structure 121. The third plurality of lock teeth attaches to a position on the first locking edge 152 such that the third plurality of lock teeth 193 interacts with the first plurality of lock teeth 191 of the first anchor mortise 171 when the first lock plate tenon structure 121 inserts into the first anchor mortise 171. The interaction between the third plurality of lock teeth 193 and the first plurality of lock teeth 191 releasably locks the first lock plate tenon structure 121 into a fixed position within the first anchor mortise 171.

The second guide structure 161 forms the leading structure of the second lock plate tenon structure 122. By leading structure is meant that the second guide structure 161 is the first element of the second lock plate tenon structure 122 that inserts into the second anchor mortise 172 of the anchor plat disk 141 of the anchor plate structure 112. The second guide structure 161 aligns the second lock plate tenon structure 122 with the second anchor mortise 172 such that the second locking edge 162 aligns with the locking structure of the second anchor mortise 172.

The second locking edge 162 is the edge of the second lock plate tenon structure 122 that is distal from the lock plate structure 123. The second locking edge 162 is the structure of the second lock plate tenon structure 122 that detachably locks the second lock plate tenon structure 122 into a fixed position within the second anchor mortise 172.

The second relief slot 163 is a slit that is formed through the congruent ends of the disk structure of the lock plate structure 123. The second relief slot 163 aligns with the edge of the second guide structure 161. The second relief slot 163 provides a flexibility to the second guide structure 161 that allows the second guide structure 161 to bend as the second guide structure 161 aligns with the locking structure of the second anchor mortise 172.

The fourth plurality of lock teeth 194 is a set of teeth that are formed on the second locking edge 162 of the second lock plate tenon structure 122. The fourth plurality of lock teeth 194 attaches to a position on the second locking edge 162 such that the fourth plurality of lock teeth 194 interacts with the third plurality of lock teeth 193 of the second anchor mortise 172 when the second lock plate tenon structure 122 inserts into the second anchor mortise 172. The interaction between the fourth plurality of lock teeth 194 and the third plurality of lock teeth 193 releasably locks the second lock plate tenon structure 122 into a fixed position within the second anchor mortise 172.

The lock plate structure 123 forms the grip used to insert the lock plate structure 102 into the base plate structure 101. The first lock plate tenon structure 121 attaches to the lock plate structure 123 to form a lateral disk structure. The second lock plate tenon structure 122 attaches to the lock plate structure 123 to form a lateral disk structure. The lock plate structure 123 forms the physical structure that presses the suture 103 into the anchor plate structure 112 of the base plate structure 101. The lock plate structure 123 is a disk shaped structure. The lock plate structure 123 comprises a suture 103 rail 181.

The suture 103 rail 181 is a mechanical structure that attaches to the lateral face of the lock plate structure 123 of the lock plate structure 102. The suture 103 rail 181 is positioned between the first lock plate tenon structure 121 and the second lock plate tenon structure 122. The suture 103 rail 181 is geometrically similar to the suture 103 notch 142 of the anchor plate structure 112 such that the suture 103 rail 181 pressure flush against the suture 103 notch 142. The suture 103 rail 181 applies the frictional pressure against the suture 103 such that the suture 103 maintains a fixed position between the suture 103 rail 181 and the suture 103 notch 142.

The suture 103 rail 181 further comprises an exterior surface thread structure 182. The exterior surface thread structure 182 comprises a plurality of ledge structures. Each ledge structure selected from the plurality of ledge structures forms a non-Euclidean prism structure. Each ledge structure selected from the plurality of ledges forms a non-Euclidean prism shape. Each ledge structure selected from the plurality of ledges is formed on the exterior non-Euclidean surface of the suture 103 rail 181. The form factor of any initially selected ledge structure is identical to the form factor of any subsequently selected ledge structure. The center axis of any initially selected ledge structure is parallel to the center axis of any subsequently selected ledge structure. The center axes of the plurality of ledge structure are evenly spaced.

Each ledge structure selected from the plurality of ledge structures that form the suture 103 rail 181 is associated with a negative space selected from the plurality of negative spaces that form the suture 103 notch 142. Each ledge structure is geometrically similar its associated negative space. The suture rail 181 aligns with the suture 103 notch 142 such that the suture 103 rail 181 inserts into the suture 103 notch 142 with a tight fit. Each selected ledge structure inserts into its associated negative space such that the center axis of each selected ledge structure aligns with the center axis of the associated negative space. The joining suture 103 rail 181 and the suture 103 notch 142 forms an interlocking structure that captures the suture 103 between the suture 103 rail 181 and the suture 103 notch 142.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Barrier: As used in this disclosure, a barrier is a physical obstacle that forms a boundary between a first space and a second space. The barrier prevents the passage of an object between the first space and the second space.

Boundary Structure: As used in this disclosure, a boundary structure is a barrier that separates a first object from a second object such that the second object cannot damage the first object.

Cant: As used in this disclosure, a cant is an angular deviation from one or more reference lines (or planes) such as a vertical line (or plane) or a horizontal line (or plane).

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Clamp: As used in this disclosure, a clamp refers to a structure that temporarily fastens a first structure to a second structure such that both the clamp and the first structure are removable from the second structure.

Composite Prism: As used in this disclosure, a composite prism refers to a structure that is formed from a plurality of structures selected from the group consisting of a prism structure and a pyramid structure. The plurality of selected structures may or may not be truncated. The plurality of prism structures are joined together such that the center axes of each of the plurality of structures are aligned. The congruent ends of any two structures selected from the group consisting of a prism structure and a pyramid structure need not be geometrically similar.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Cord: As used in this disclosure, a cord is a long, thin, flexible, and prism shaped string, line, rope, or wire. Cords are made from yarns, piles, or strands of material that are braided or twisted together or from a monofilament (such as fishing line). Cords have tensile strength but are too flexible to provide compressive strength and are not suitable for use in pushing objects. String, line, cable, yarn, and rope are synonyms for cord. This definition further includes textile webbings as a type of cord.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Nature: As used in this disclosure, an elastic nature refers to a flexible structure that returns to its relaxed shape after the flexible structure has been deformed. Environment: As used in this disclosure, an environment refers to the physical conditions surrounding an object. The term environment is often limited to the physical conditions that the object interacts with.

Euclidean Surface: As used in this disclosure, a Euclidean surface refers to a two-dimensional plane that is formed without a curvature. By without a curvature is meant that the shortest distance between any two points on a Euclidean surface forms a line that remains on the Euclidean surface.

Exterior: As used in this disclosure, the exterior is used as a relational term that implies that an object is not contained within the boundary of a structure or a space.

Fitted: As used in this disclosure, the term fitted refers to two geometrically similar structures wherein the smaller geometrically similar structure inserts into the larger geometrically similar structure.

Flexible: As used in this disclosure, flexible refers to an object or material that will deform when a force is applied to it but that will not necessarily return to its original shape when the deforming force is removed.

Flush: As used in this disclosure, the term flush is used to describe the alignment of a first surface and a second surface to form a single structure selected from the group consisting of a Euclidean plane and a non-Euclidean plane.

Form Factor: As used in this disclosure, the term form factor refers to the size and shape of an object.

Friction: As used in this disclosure, friction refers to a force that occurs between two objects that are in relative motion while in contact with each other. The force resists the relative motion of the two objects. More technically, friction refers to an exchange of energy between two objects that are in contact with each other that converts the energy of a directed relative motion between the two objects into randomly directed motions of the molecules that form both objects.

Force: As used in this disclosure, a force refers to a net (or unopposed) measurable interaction that changes the direction of motion of an object, the velocity of motion of an object, the momentum of an object, or the stress within an object. The term work refers to a measure of the amount of energy that is transferred through the application of a force over a distance. The term power refers to a measure of the amount of energy that is transferred over a period of time.

Friction: As used in this disclosure, friction refers to a force that occurs between two objects that are in relative motion while in contact with each other. The force resists the relative motion of the two objects. More technically, friction refers to an exchange of energy between two objects that are in contact with each other that converts the energy of a directed relative motion between the two objects into randomly directed motions of the molecules that form both objects.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1. By the term essentially geometrically similar is meant that the primary shapes of two objects are geometrically similar except that there are functional items (such as fastening devices) associated with the primary shape may not maintain the ratio for geometric similarity. By the term roughly geometrically similar is meant that the form factors between the primary shape of the two objects can vary by a factor of up to 10% when the two objects are normalized to be roughly geometrically identical.

Inelastic Nature: As used in this disclosure, an inelastic nature refers to a flexible structure that maintains its new shape after the flexible structure has been deformed.

Interior: As used in this disclosure, the interior is used as a relational term that implies that an object is contained within the boundary of a structure or a space.

Latch: As used in this disclosure, a latch is a fastening or locking mechanism. The use of the term latch does not necessarily but often implies the insertion of an object into a notch or cavity.

Lateral Disk Structure: As used in this disclosure, a lateral plate structure refers to the juxtaposition of a first lateral face of a first disk-shaped structure to a second lateral face of a second disk-shaped structure such that: a) the center axes of the first disk and the second disk are parallel; and, b) the congruent ends of the first disk are parallel to the congruent ends of the second disk. The span of the length of the center axes of the first disk and the second disk need not be equal. The form factor of the congruent ends of the first disk and the second disk need not be geometrically similar.

Lateral Prism Structure: As used in this disclosure, a lateral prism structure refers to the juxtaposition of a first lateral face of a first prism structure to a second lateral face of a second prism structure such that: a) the center axes of the first prism and the second prism are parallel; and, b) the congruent ends of the first prism are parallel to the congruent ends of the second prism. The span of the length of the center axes of the first prism and the second prism need not be equal. The form factor of the congruent ends of the first prism and the second prism need not be geometrically similar.

Ledge: As used in this disclosure, a ledge is a first plate structure that projects away from a second plate structure. A ledge that projects away from, or overhangs, the second plate structure in the manner of a cantilever is referred to as an undercut ledge.

Lock: As used in this disclosure, a lock is a fastening device that fixes the position of a first object relative to a second object such that the first object and the second object are subsequently releasable.

Mortise: As used in this disclosure, a mortise is a prism-shaped negative space formed in an object that is designed to receive a geometrically similar object referred to as a tenon.

Negative Space: As used in this disclosure, negative space is a method of defining an object through the use of open or empty space as the definition of the object itself, or, through the use of open or empty space to describe the boundaries of an object.

Non-Euclidean Line: A non-Euclidean line is a line that is formed with a curvature. Specifically, a non-Euclidean line comprises a set of points wherein the path of the span of the shortest distance between at least two points selected from the line does not lie on the path of the line itself. When a non-Euclidean line forms a section of the perimeter of a structure, the non-Euclidean line is often called a non-Euclidean edge.

Non-Euclidean Plane: As used in this disclosure, a non-Euclidean plane (or non-Euclidean surface) is a geometric plane that is formed with a curvature such that: a) two parallel lines will intersect somewhere in the planar surface; or, b) the span of the perpendicular distance between two parallel lines will vary as a function of the position of the plane; or, c) the minimum distance between two points on the non-Euclidean plane as measured along the non-Euclidean plane is greater than the absolute minimum distance between the same two points. In many geometries, the statements (a) and (b) can be considered identical statements. A non-Euclidean plane is said to form a roughly Euclidean surface (or plane) when the span of the minimum distance between two points on the non-Euclidean plane as measured along the non-Euclidean plane is less than or equal to 1.1 times the absolute minimum distance between the same two points.

Non-Euclidean Prism: As used in this disclosure, a non-Euclidean prism is a prism structure wherein the center axis of the prism lies on a non-Euclidean plane or is otherwise formed with a curvature.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different.

Notch: As used in this disclosure, a notch is: 1) an indentation or negative space formed in an edge; or 2) a cavity or aperture formed within a surface.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Pan: As used in this disclosure, a pan is a hollow and prism-shaped containment structure. The pan has a single open face. The open face of the pan is often, but not always, the superior face of the pan. The open face is a surface selected from the group consisting of: a) a congruent end of the prism structure that forms the pan; and, b) a lateral face of the prism structure that forms the pan. A semi-enclosed pan refers to a pan wherein the closed end of prism structure of the pan and/or a portion of the closed lateral faces of the pan are open.

Patient: As used in this disclosure, a patient is a person who is designated to receive a medical treatment, therapy, or service. The term patient may be extended to an animal when used within the context of the animal receiving veterinary treatment or services.

Pedestal: As used in this disclosure, a pedestal is an intermediary load bearing structure that forms a load path between two objects or structures.

Perimeter: As used in this disclosure, a perimeter is one or more curved or straight lines that bounds an enclosed area on a plane or surface. The perimeter of a circle is commonly referred to as a circumference.

Pressure: As used in this disclosure, pressure refers to a measure of force per unit area.

Primary Shape: As used in this disclosure, the primary shape refers to a description of the rough overall geometric shape of an object that is assembled from multiple components or surfaces. Use Roughly Primary Structure: As used in this disclosure, a primary structure refers to the component of an object that the other components attach to. The primary structure is also called the base structure.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Protective Barrier: As used in this disclosure, a protected barrier is a boundary structure. The boundary structure forms a barrier that separates a first object from a second object such that the second object cannot damage the first object.

Raw Edge: As used in this disclosure, a raw edge refers to one of two edges that are formed when a slit is cut through the face of the sheeting. The one or more ends of the slit are called the termination points.

Relaxed Shape: As used in this disclosure, a structure is considered to be in its relaxed state when no shear, strain, or torsional forces are being applied to the structure.

Rigid Structure: As used in this disclosure, a rigid structure is a solid structure formed from an inelastic material that resists changes in shape. A rigid structure will permanently deform as it fails under a force.

Roughly: As used in this disclosure, roughly refers to a comparison between two objects. Roughly means that the difference between one or more parameters of the two compared objects are not significantly different.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Slit: As used in this disclosure, a slit is a long narrow cut, aperture, or opening that is formed in or through a surface.

Stack: As used in this disclosure, a stack refers to a collection of prism-shaped objects that are stored such that the congruent ends of each of the prism-shaped objects are placed against each other such that the congruent ends are parallel to each other. The term stack often implies that the congruent ends of the prism-shaped objects are horizontally oriented.

Teeth: As used in this disclosure, the teeth refer to a plurality of working elements of a tool that interact with a pawl or with other teeth to perform the function of the tool. The teeth found on gears is a common example of the use of teeth. An individual working element selected form the plurality of working elements is called a tooth.

Tenon: As used in this disclosure, a tenon is a prism-shaped structure that fits into a mortise such that the tenon is secured to the mortise. The tenon is geometrically similar to the mortise.

Therapeutic: As used in this disclosure, therapeutic is an adjective that refers to a medical, ameliorative, or hygienic substance, process, procedure, or device.

Tight Fit: As used in this disclosure, a tight fit refers to the insertion of a first object into a second object such that there is not a lot of space between the first object and the second object. By not a lot of space is meant that friction occurs when the first object moves within the second object.

U-Shaped Structure: As used in this disclosure, a U-shaped structure is a type of offset composite prism structure. The U-shaped structure is a three sided structure comprising a crossbeam, a first arm, and a second arm. In a U-shaped structure, the first arm and the second arm project away from the crossbeam: 1) in the same direction; 2) at a roughly perpendicular angle to the crossbeam, and, 3) the span of length of the first arm roughly equals the span of length of the second arm. An illiterate U-shaped structure refers to a U-shaped structure wherein the span of the length of the first arm differs from the span of the length of the second arm by more than 10 percent. A guided U-shaped structure refers to a U-shaped structure that has: a) the first arc formed by the interior cant formed between the first arm and the crossbeam is greater than or equal to 100 degrees; b) a second arc formed by the interior cant formed between the second arm and the crossbeam is greater than or equal to 100 degrees; and, c) the first arc and the second arc are roughly equal.

With respect to the above description, it is to be realized that the optimum dimensional relationship for the various components of the invention described above and in FIGS. 1 through 7 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A wound closure system comprising a base plate structure, a lock plate structure, and a suture;

wherein the lock plate structure secures the suture to the base plate structure;

wherein the wound closure system is a therapeutic structure;

wherein the wound closure system is an instrument that applies a suture;

wherein the suture is a cord that inserts through the base plate structure;

wherein the lock plate structure presses the suture against the base plate structure to form a tight fit;

wherein the base plate structure comprises a ledge plate structure and an anchor plate structure;

wherein a congruent end of a disk structure of the anchor plate structure permanently attaches to the congruent end of the disk structure of the ledge plate structure.

2. The wound closure system according to claim 1
wherein the lock plate structure inserts into the base plate structure;
wherein the lock plate structure secures the suture to the base plate structure;
wherein the base plate structure has the shape of a stack of disk shaped structures.

3. The wound closure system according to claim 2
wherein the lock plate structure has an irregular shape;
wherein the lock plate structure is formed as a disk;
wherein the lock plate structure inserts into the base plate structure;
wherein the forms factor of the lock plate structure fits flush against the base plate structure;
wherein the lock plate structure inserts into the base plate structure such that the suture inserts into the lock plate structure and the base plate structure;
wherein the suture inserts between the base plate structure and the lock plate structure;
wherein the suture is held in a fixed position relative to the lock plate structure and the base plate structure by frictional forces.

4. The wound closure system according to claim 1
wherein the lock plate structure comprises a first lock plate tenon structure, a second lock plate tenon structure, and a lock plate structure;
wherein the first lock plate tenon structure attaches to the lock plate structure to form a lateral disk structure;
wherein the second lock plate tenon structure attaches to the lock plate structure to form a lateral disk structure.

5. The wound closure system according to claim 4
wherein the ledge plate structure has a disk shape;
wherein the anchor plate structure has a disk shape;
wherein the span of the length of the perimeter of the congruent ends of the disk structure of the anchor plate structure is lesser than the span of the length of the perimeter of the congruent ends of the disk structure of the ledge plate structure;
wherein the anchor plate structure forms the structure of the base plate structure that receives the lock plate structure for attachment.

6. The wound closure system according to claim 5
wherein the anchor plate structure comprises an anchor plate disk, a suture notch, and a suture eye;
wherein the anchor plate disk is a disk shaped structure;
wherein the anchor plate disk forms the physical disk structure of the anchor plate structure;
wherein the anchor plate disk permanently attaches to the congruent end of the disk structure of the ledge plate structure;
wherein the anchor plate disk further comprises a first anchor mortise and a second anchor mortise;
wherein the first anchor mortise is a mortise that is formed into the lateral face of the disk structure of the anchor plate structure;
wherein the first anchor mortise is sized such that the first lock plate tenon structure of the lock plate structure inserts into the first anchor mortise;
wherein the first anchor mortise is formed with a locking mechanism that locks the ledge plate structure into a fixed position relative to the first anchor mortise;
wherein the first anchor mortise further comprises a first plurality of lock teeth;
wherein the first plurality of lock teeth is a set of teeth that are formed on the interior surface of the first anchor mortise;
wherein the first plurality of lock teeth forms the locking mechanism of the first anchor mortise;
wherein the second anchor mortise is a mortise that is formed into the lateral face of the disk structure of the anchor plate structure;
wherein the second anchor mortise is sized such that the second lock plate tenon structure of the lock plate structure inserts into the second anchor mortise;
wherein the second anchor mortise is formed with a locking mechanism that locks the ledge plate structure into a fixed position relative to the second anchor mortise;
wherein the second anchor mortise further comprises a second plurality of lock teeth;
wherein the second plurality of lock teeth is a set of teeth that are formed on the interior surface of the second anchor mortise;
wherein the second plurality of lock teeth forms the locking mechanism of the second anchor mortise;
wherein the suture eye is a negative space that is formed through the congruent ends of the disk structure of the ledge plate structure;
wherein the suture inserts through the suture eye into the suture notch;
wherein the suture notch is a notch that is formed in the lateral face of the disk structure of the anchor plate disk;
wherein the suture notch is positioned between the first anchor mortise and the second anchor mortise;
wherein the suture is pressed by the lock plate structure into the suture notch of the anchor plate structure.

7. The wound closure system according to claim 6
wherein the first lock plate tenon structure is a tenon that secures the lock plate structure to the base plate structure;
wherein the first lock plate tenon structure inserts into the first anchor mortise of the anchor plate structure of the base plate structure;
wherein the first lock plate tenon structure is a locking structure;
wherein the first lock plate tenon structure interacts with the first anchor mortise such that the first lock plate tenon structure detachably attaches to the first anchor mortise;
wherein the first lock plate tenon structure locks the lock plate structure into a fixed position relative to the base plate structure and the suture;
wherein the second lock plate tenon structure is a tenon that secures the lock plate structure to the base plate structure;
wherein the second lock plate tenon structure inserts into the second anchor mortise of the anchor plate structure of the base plate structure;
wherein the second lock plate tenon structure is a locking structure;
wherein the second lock plate tenon structure interacts with the second anchor mortise such that the second lock plate tenon structure detachably attaches to the second anchor mortise;
wherein the second lock plate tenon structure locks the lock plate structure into a fixed position relative to the base plate structure and the suture.

8. The wound closure system according to claim 7
wherein the lock plate structure forms the grip used to insert the lock plate structure into the base plate structure;

wherein the lock plate structure forms the physical structure that presses the suture into the anchor plate structure of the base plate structure;
wherein the lock plate structure is a disk shaped structure;
wherein the lock plate structure comprises a suture rail;
wherein the suture rail is a mechanical structure that attaches to the lateral face of the lock plate structure of the lock plate structure;
wherein the suture rail is positioned between the first lock plate tenon structure and the second lock plate tenon structure;
wherein the suture rail is geometrically similar to the suture notch of the anchor plate structure such that the suture rail pressure flush against the suture notch;
wherein the suture rail applies the frictional pressure against the suture such that the suture maintains a fixed position between the suture rail and the suture notch.

9. The wound closure system according to claim 8
wherein the first lock plate tenon structure comprises a first guide structure, a first locking edge, a first relief slot, and a third plurality of lock teeth;
wherein the first guide structure forms the leading structure of the first lock plate tenon structure;
wherein by leading structure is meant that the first guide structure is the first element of the first lock plate tenon structure that inserts into the first anchor mortise of the anchor plate disk of the anchor plate structure;
wherein the first guide structure aligns the first lock plate tenon structure with the first anchor mortise such that the first locking edge aligns with the locking structure of the first anchor mortise;
wherein the first locking edge is the edge of the first lock plate tenon structure that is distal from the second lock plate tenon structure;
wherein the first locking edge is the structure of the first lock plate tenon structure that detachably locks the first lock plate tenon structure into a fixed position within the first anchor mortise;
wherein the first relief slot is a slit that is formed through the congruent ends of the disk structure of the lock plate structure;
wherein the first relief slot aligns with the edge of the first guide structure;
wherein the first relief slot provides a flexibility to the first guide structure that allows the first guide structure to bend as the first guide structure aligns with the locking structure of the first anchor mortise;
wherein the third plurality of lock teeth is a set of teeth that are formed on the first locking edge of the first lock plate tenon structure;
wherein the third plurality of lock teeth attaches to a position on the first locking edge such that the third plurality of lock teeth interacts with the first plurality of lock teeth of the first anchor mortise when the first lock plate tenon structure inserts into the first anchor mortise;
wherein the interaction between the third plurality of lock teeth and the first plurality of lock teeth releasably locks the first lock plate tenon structure into a fixed position within the first anchor mortise.

10. The wound closure system according to claim 9
wherein the second lock plate tenon structure comprises a second guide structure, a second locking edge, a second relief slot, and a fourth plurality of lock teeth;
wherein the second guide structure forms the leading structure of the second lock plate tenon structure;
wherein by leading structure is meant that the second guide structure is the first element of the second lock plate tenon structure that inserts into the second anchor mortise of the anchor plate disk of the anchor plate structure;
wherein the second guide structure aligns the second lock plate tenon structure with the second anchor mortise such that the second locking edge aligns with the locking structure of the second anchor mortise;
wherein the second locking edge is the edge of the second lock plate tenon structure that is distal from the lock plate structure;
wherein the second locking edge is the structure of the second lock plate tenon structure that detachably locks the second lock plate tenon structure into a fixed position within the second anchor mortise;
wherein the second relief slot is a slit that is formed through the congruent ends of the disk structure of the lock plate structure;
wherein the second relief slot aligns with the edge of the second guide structure;
wherein the second relief slot provides a flexibility to the second guide structure that allows the second guide structure to bend as the second guide structure aligns with the locking structure of the second anchor mortise;
wherein the fourth plurality of lock teeth is a set of teeth that are formed on the second locking edge of the second lock plate tenon structure;
wherein the fourth plurality of lock teeth attaches to a position on the second locking edge such that the fourth plurality of lock teeth interacts with the third plurality of lock teeth of the second anchor mortise when the second lock plate tenon structure inserts into the second anchor mortise;
wherein the interaction between the fourth plurality of lock teeth and the third plurality of lock teeth releasably locks the second lock plate tenon structure into a fixed position within the second anchor mortise.

11. The wound closure system according to claim 10
wherein the suture notch further comprises an interior surface thread structure;
wherein the suture rail further comprises an exterior surface thread structure;
wherein the interior surface thread structure comprises a plurality of negative spaces;
wherein the exterior surface thread structure comprises a plurality of ledge structures;
wherein each ledge structure selected from the plurality of ledge structures that form the suture rail is associated with a negative space selected from the plurality of negative spaces that form the suture notch;
wherein each ledge structure is geometrically similar its associated negative space;
wherein the suture rail aligns with the suture notch such that the suture rail inserts into the suture notch with a tight fit;
wherein each selected ledge structure inserts into its associated negative space such that the center axis of each selected ledge structure aligns with the center axis of the associated negative space;
wherein the joining suture rail and the suture notch forms an interlocking structure.

* * * * *